(12) United States Patent
Lhermitte et al.

(10) Patent No.: US 7,790,901 B2
(45) Date of Patent: Sep. 7, 2010

(54) PROCESS FOR THE PREPARATION OF A 2-PYRIDYLETHYLCARBOXAMIDE DERIVATIVE

(75) Inventors: Frédéric Lhermitte, Saint Symphorien d'Ozon (FR); Pierre-Yves Coqueron, Lyons (FR); Philippe Desbordes, Lyons (FR); Thomas Himmler, Odenthal (DE)

(73) Assignee: Bayer Cropscience S.A. (FR)

( * ) Notice: Subject to any disclaimer, the term of this patent is extended or adjusted under 35 U.S.C. 154(b) by 485 days.

(21) Appl. No.: 11/793,561

(22) PCT Filed: Dec. 19, 2005

(86) PCT No.: PCT/EP2005/056895

§ 371 (c)(1),
(2), (4) Date: Jun. 19, 2007

(87) PCT Pub. No.: WO2006/067103

PCT Pub. Date: Jun. 29, 2006

(65) Prior Publication Data

US 2008/0086008 A1 Apr. 10, 2008

(30) Foreign Application Priority Data

Dec. 21, 2004 (EP) .................... 04356203

(51) Int. Cl.
*C07D 213/127* (2006.01)
(52) U.S. Cl. ............... 546/337; 546/329; 546/330; 546/335; 546/336
(58) Field of Classification Search ............. 546/329, 546/330, 335, 336, 337
See application file for complete search history.

(56) References Cited

FOREIGN PATENT DOCUMENTS

| DE | 1 034 644 | 7/1958 |
| EP | 0 061 836 | 10/1982 |
| WO | WO01/11965 | 2/2001 |
| WO | WO 2004/016088 | 2/2004 |

OTHER PUBLICATIONS

Hashimoto, M. et al., "A Facile Synthesis of Substituted Methylamides from Acetoxymethylamides," 7 Chemistry Express 1, pp. 65-68 (1992) ISSN 0911-9566.

*Primary Examiner*—Patricia L Morris
(74) *Attorney, Agent, or Firm*—Ostrolenk Faber LLP

(57) ABSTRACT

Process for the preparation of a N-[2-(2-pyridinyl)ethyl]carboxamide derivative of general formula (I) or a salt thereof

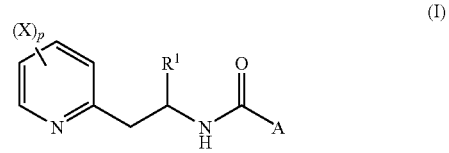

Intermediate of general formula (II)

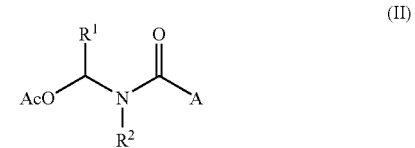

Intermediate of general formula (III).

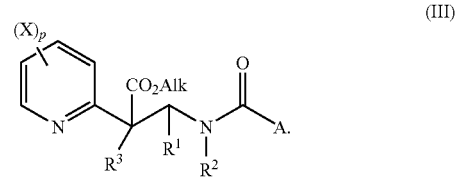

17 Claims, No Drawings

PROCESS FOR THE PREPARATION OF A 2-PYRIDYLETHYLCARBOXAMIDE DERIVATIVE

CROSS REFERENCE TO RELATED APPLICATION(S)

The present application is a 35 U.S.C. §371 national phase conversion of PCT/EP2005/056895 filed Dec. 19, 2005, which claims priority of European Application No. 04356203.2 filed Dec. 21, 2004.

The present invention relates to a novel process for the preparation of N-[2-(2-pyridinyl)ethyl]carboxamide derivative which is useful as pesticide compound, starting with a halogenobenzoyl derivative to produce a N-acetoxymethyl-carboxamide derivative and then coupling it with a 2-pyridyl acetate derivative.

Patent application WO 2004/016088 discloses the preparation of N-[2-(2-pyridinyl)ethyl]benzamide derivatives starting from 2-halogenopyridine derivatives to produce 2-ethylaminopyridine derivatives and then coupling these 2-ethylaminopyridine derivatives with a halogenobenzoyl derivative.

The process disclosed in this patent application presents the drawback in that one of the step of this process consists in the reduction of a 2-methylcyanopyridine derivative to produce a 2-ethylaminopyridine derivative. Such a step is difficult and its yield is not acceptable at an industrial scale.

We have now found an alternative method to prepare N-[2-(2-pyridinyl)ethyl]carboxamide derivative which overcomes these problems and which is applicable to industrial scale operation.

Accordingly, the present invention relates to a process for the preparation of a N-[2-(2-pyridinyl)ethyl]carboxamide derivative of general formula (I) or a salt thereof

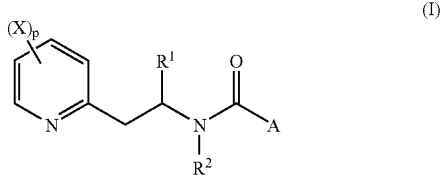

(I)

in which:

p is an integer equal to 1, 2, 3 or 4;

X is the same or different and is a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a (N—$C_1$-$C_8$-alkyl)oxycarbamoyl, a $C_1$-$C_8$-alkoxycarbamoyl, a (N—$C_1$-$C_8$-alkyl)-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkyl-sulphonyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl or a phenylamino;

$R^1$ is a hydrogen atom, a $C_1$-$C_8$-alkyl, a $C_1$-$C_8$-halogenoalkyl having 1 to 5 halogen atoms or a $C_1$-$C_8$-alkoxycarbonyl;

$R^2$ is a hydrogen atom or a cyclopropyl group; and

A represents a phenyl group or a 5-, 6- or 7-membered non-fused heterocycle with one, two or three heteroatoms which may be the same or different, the heterocycle being linked by a carbon atom; each of this group being optionally substituted by one or more substituents chosen independently of each other as being a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms or a $C_1$-$C_8$-alkylsulfonamide;

as to the N-oxides of the 2-pyridine thereof;

said process comprising:

(A)-a first step according to reaction scheme 1:

Scheme 1

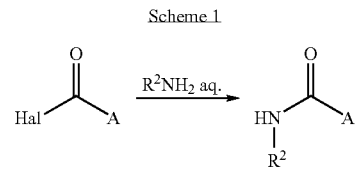

in which:

A and $R^2$ are as defined above; and

Hal represents a halogen atom;

comprising the reaction of a halogenobenzoyl derivative with aqueous $R^2NH_2$, in a $R^2NH_2$ aq./halogenobenzoyl derivative molar ratio of from 1 to 10, to provide a carboxamide derivative;

(B)-a second step according to reaction scheme 2:

Scheme 2

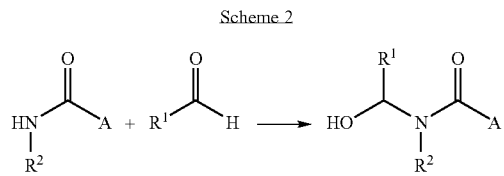

in which $R^1$, $R^2$ and A are as defined above; comprising the reaction of a carboxamide derivative obtained in step one with an aldehyde group in an aldehyde group/carboxamide derivative molar ratio of from 1 to 10, in a polar solvent, at a temperature of from 20° C. to reflux, to provide a N-hydroxymethylcarboxamide derivative;

(C)-a third step according to reaction scheme 3:

Scheme 3

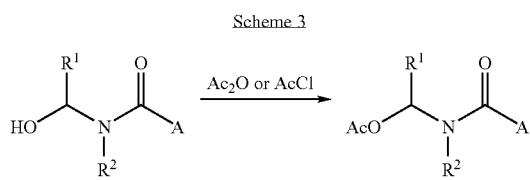

in which:
$R^1$, $R^2$ and A are as defined above; and
Ac represents an acetyl group;

comprising the reaction of a N-hydroxymethylcarboxamide derivative obtained in step two with acetic anhydride ($Ac_2O$) or acetyl chloride (AcCl) in a $Ac_2O$ or AcCl/N-hydroxymethylcarboxamide derivative molar ratio of from 1 to 10, in an organic solvent, in the presence of a mineral or organic base, to provide a N-acetoxymethylcarboxamide derivative;

(D)-a fourth step according to reaction scheme 4:

Scheme 4

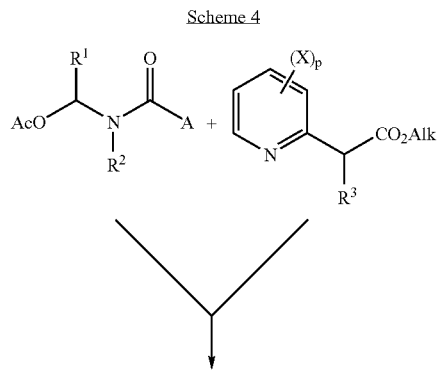

-continued

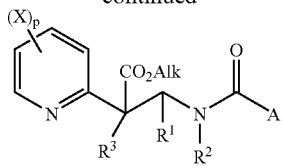

in which:
X, $R^1$, $R^2$, p and A are as defined above;
Ac represents an acetyl group;
$R^3$ represents a hydrogen atom or $CO_2Alk$; and
Alk represents a $C_1$-$C_8$-alkyl group;

comprising the reaction of a N-acetoxymethylcarboxamide derivative obtained in step three with a 2-pyridyl acetate derivative in a N-acetoxymethylcarboxamide derivative/2-pyridyl acetate derivative molar ratio of from 1 to 5, in an organic solvent, in the presence of a base; to provide a 2-pyridylethylcarboxamide derivative;

(E)-a fifth step comprising the decarboxylation of the 2-pyridylethylcarboxamide derivative obtained in step four into a compound of general formula (I).

For the purposes of the present invention:
a halogen atom may be a bromine atom, a chlorine atom, a iodine atom or a fluorine atom. Preferably, halogen atom means chlorine atom;
carboxy means —C(=O)OH;
carbonyl means —C(=O)—;
carbamoyl means —C(=O)NH$_2$;
N-hydroxycarbamoyl means —C(=O)NHOH;
an alkyl group, an alkenyl group, and an alkynyl group as well as moieties containing these terms, can be linear or branched; and
a compound used in "catalytic quantity" means that a compound is used in an amount of 0.01 to 0.2 molar equivalent, preferably from 0.01 to 0.1 molar equivalent of the respective reagent or intermediate compound.

During the preparation of compound of general formula (I) according to the present invention, there is no need to reduce a 2-methylcyanopyridine derivative into a 2-ethylaminopyridine derivative, which increases the yield of product obtained by the process according to the present invention. Such a process can thus be used at an industrial scale.

According to the present invention, the 2-pyridyl moiety may be substituted in any position by $(X)_p$, in which X and p are as defined above. Preferably, the present invention relates to the preparation of N-[2-(2-pyridinyl)ethyl]carboxamide derivative of general formula (I) in which the different characteristics may be chosen alone or in combination as being:
as regards p, p is 1, 2 or 3. Preferably, p is 2.
as regards X, X is chosen, independently of the others, as being a halogen atom, a $C_1$-$C_8$-alkyl or a $C_1$-$C_8$-halogenoalkyl having 1 to 5 halogen atoms. More preferably, X is chosen, independently of the others, as being chlorine or $CF_3$;
as regards the positions in which the 2-pyridyl moiety is substituted by X, the 2-pyridyl moiety is substituted by X in 3- and/or in 5-position. Preferably, the 2-pryridyl moiety is substituted by X in 3- and 5-position.

According to the present invention, the "ethylamide" part of the compound of formula (I) is substituted by $R^1$ and $R^2$, $R^1$ and $R^2$ being as defined above. Preferably, the present invention relates to the preparation of N-[2-(2-pyridinyl)ethyl]benzamide derivative of general formula (I) in which the different characteristics may be chosen alone or in combination as being:
as regards $R^1$, $R^1$ is a hydrogen atom, a methyl group, $CF_3$, $CHF_2$, $CClF_2$ or $CCl_3$.

More preferably, $R^1$ is a hydrogen atom;
as regards $R^2$, $R^2$ is a hydrogen atom.

According to the present invention, A may represent a five membered ring non-fused heterocycle. Specific examples of compounds prepared according to the process of the present invention where A is a five membered heterocycle include compound of general formula (I) wherein:

* A represents a heterocycle of the general formula (A-1)

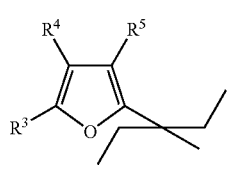

in which:
$R^3$ and $R^4$ may be the same or different and may be a hydrogen atom, a halogen atom, an amino group, a nitro group, a $C_1$-$C_4$-alkyl or a $C_1$-$C_4$-halogenoalkyl having 1 to 5 halogen atoms; and
$R^5$ may be a halogen atom, a nitro group, a $C_1$-$C_4$-alkyl or a $C_1$-$C_4$-halogenoalkyl having 1 to 5 halogen atoms.

* A represents a heterocycle of the general formula (A-2)

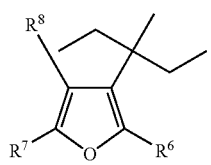

in which:
$R^6$ may be a hydrogen atom, a halogen atom, a $C_1$-$C_4$-alkyl or a $C_1$-$C_4$-halogenoalkyl having 1 to 5 halogen atoms; and
$R^7$ and $R^8$ may be the same or different and may be a hydrogen atom, a halogen atom, an amino group, a $C_1$-$C_4$-alkyl or a $C_1$-$C_4$-halogenoalkyl having 1 to 5 halogen atoms.

* A represents a heterocycle of the general formula (A-3)

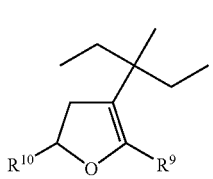

in which:
$R^9$ may be a halogen atom, a $C_1$-$C_4$-alkyl or a $C_1$-$C_4$-halogenoalkyl having 1 to 5 halogen atoms; and $R^{10}$ may be a hydrogen atom, a $C_1$-$C_4$-alkyl or a $C_1$-$C_4$-halogenoalkyl having 1 to 5 halogen atoms.

* A represents a heterocycle of the general formula (A-4)

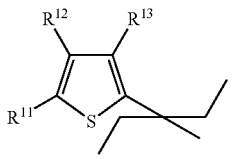

in which:
$R^{11}$ and $R^{12}$ may be the same or different and may be a hydrogen atom, a halogen atom, a $C_1$-$C_4$-alkyl, a $C_1$-$C_4$-halogenoalkyl having 1 to 5 halogen atoms, a $C_1$-$C_4$-alkylthio, a $C_1$-$C_4$-alkylsulphonyl, a phenyl optionally substituted by a halogen atom or a $C_1$-$C_4$-alkyl or a pyridyl optionally substituted by a halogen atom or a $C_1$-$C_4$-alkyl; and
$R^{13}$ may be a halogen atom, a cyano group, a $C_1$-$C_4$-alkyl, a $C_1$-$C_4$-halogenoalkyl having 1 to 5 halogen atoms or a $C_1$-$C_4$-halogenoalkoxy having 1 to 5 halogen atoms.

* A represents a heterocycle of the general formula (A-5)

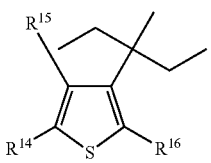

in which:
$R^{14}$ and $R^{15}$ may be the same or different and may be a hydrogen atom, a halogen atom, a $C_1$-$C_4$-alkyl, a $C_1$-$C_4$-alkyloxy or a $C_1$-$C_4$-halogenoalkyl having 1 to 5 halogen atoms; and
$R^{16}$ may be a hydrogen atom, a halogen atom, a $C_1$-$C_4$-alkyl or a $C_1$-$C_4$-halogenoalkyl having 1 to 5 halogen atoms.

* A represents a heterocycle of the general formula (A-6)

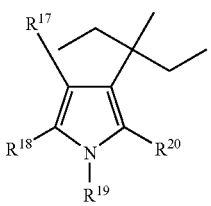

in which:
$R^{17}$ may be a hydrogen atom, a halogen atom, a cyano group, a $C_1$-$C_4$-alkyl or a $C_1$-$C_4$-halogenoalkyl having 1 to 5 halogen atoms;
$R^{18}$ and $R^{20}$ may be the same or different and may be a hydrogen atom, a halogen atom, a $C_1$-$C_4$-alkyl or a $C_1$-$C_4$-halogenoalkyl having 1 to 5 halogen atoms; and
$R^{19}$ may be a hydrogen atom, a cyano group, a $C_1$-$C_4$-alkyl, a $C_1$-$C_4$-halogenoalkyl having 1 to 5 halogen atoms, a $C_1$-$C_4$-alkoxy-$C_1$-$C_4$-alkyl, a hydroxy-$C_1$-$C_4$-alkyl, a $C_1$-$C_4$-alkylsulphonyl, a di($C_1$-$C_4$-alkyl)aminosulphonyl, a $C_1$-$C_6$-alkylcarbonyl, a phenylsulphonyl optionally substituted by a halogen atom or a $C_1$-$C_4$-alkyl, or a benzoyl optionally substituted by a halogen atom or a $C_1$-$C_4$-alkyl.

* A represents a heterocycle of the general formula (A-7)

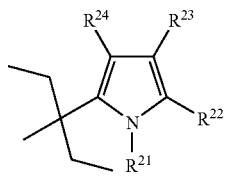

(A-7)

in which:
$R^{21}$ may be a hydrogen atom, a cyano group, a $C_1$-$C_4$-alkyl, a $C_1$-$C_4$-halogenoalkyl having 1 to 5 halogen atoms, a $C_1$-$C_4$-alkoxy-$C_1$-$C_4$-alkyl, a hydroxy-$C_1$-$C_4$-alkyl, a $C_1$-$C_4$-alkylsulphonyl, a di($C_1$-$C_4$-alkyl)aminosulphonyl, a $C_1$-$C_6$-alkylcarbonyl, a phenylsulphonyl optionally substituted by a halogen atom or a $C_1$-$C_4$-alkyl, or a benzoyl optionally substituted by a halogen atom or a $C_1$-$C_4$-alkyl; and $R^{22}$, $R^{23}$ and $R^{24}$ may be the same or different and may be a hydrogen atom, a halogen atom, a cyano group, a $C_1$-$C_4$-alkyl, a $C_1$-$C_4$-halogenoalkyl having 1 to 5 halogen atoms or a $C_1$-$C_4$-alkylcarbonyl.

* A represents a heterocycle of the general formula (A-8)

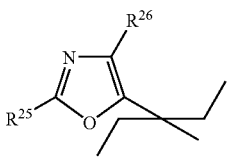

(A-8)

in which:
$R^{25}$ may be a hydrogen atom or a $C_1$-$C_4$-alkyl; and
$R^{26}$ may be a halogen atom, a $C_1$-$C_4$-alkyl or a $C_1$-$C_4$-halogenoalkyl having 1 to 5 halogen atoms.

* A represents a heterocycle of the general formula (A-9)

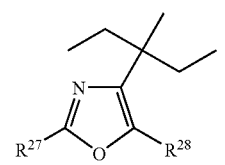

(A-9)

in which:
$R^{27}$ may be a hydrogen atom or a $C_1$-$C_4$-alkyl; and
$R^{28}$ may be a halogen atom, a $C_1$-$C_4$-alkyl, a $C_1$-$C_4$-halogenoalkyl having 1 to 5 halogen atoms or a phenyl optionally substituted by a halogen atom or a $C_1$-$C_4$-alkyl.

* A represents a heterocycle of the general formula (A-10)

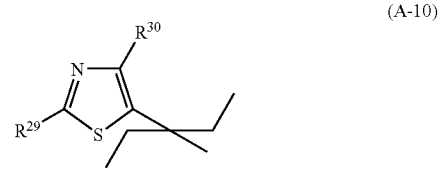

(A-10)

in which:
$R^{29}$ may be a hydrogen atom, a halogen atom, an amino group, a cyano group, a $C_1$-$C_4$-alkylamino, a di-($C_1$-$C_4$-alkyl)amino, a $C_1$-$C_4$-alkyl, a $C_1$-$C_4$-halogenoalkyl having 1 to 5 halogen atoms or a phenyl optionally substituted by a halogen atom or a $C_1$-$C_4$-alkyl; and
$R^{30}$ may be a halogen atom, a $C_1$-$C_4$-alkyl or a $C_1$-$C_4$-halogenoalkyl having 1 to 5 halogen atoms.

* A represents a heterocycle of the general formula (A-11)

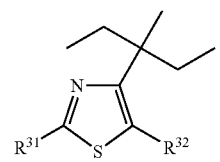

(A-11)

in which:
$R^{31}$ may be a hydrogen atom, a halogen atom, an amino group, a cyano group, a $C_1$-$C_4$-alkylamino, a di-($C_1$-$C_4$-alkyl)amino, a $C_1$-$C_4$-alkyl or a $C_1$-$C_4$-halogenoalkyl having 1 to 5 halogen atoms; and
$R^{32}$ may be a halogen atom, a $C_1$-$C_4$-Alkyl or a $C_1$-$C_4$-halogenoalkyl having 1 to 5 halogen atoms.

* A represents a heterocycle of the general formula (A-12)

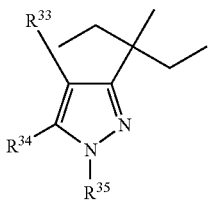

(A-12)

in which:
$R^{33}$ may be a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl group or an aminocarbonyl-$C_1$-$C_4$-alkyl;
$R^{34}$ may be a hydrogen atom, a halogen atom, a cyano group, a nitro group, a $C_1$-$C_4$-alkyl, a $C_1$-$C_4$-alkoxy or a $C_1$-$C_4$-alkylthio; and
$R^{35}$ may be a hydrogen atom, a phenyl, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl or a $C_1$-$C_4$-halogenoalkoxy-$C_1$-$C_4$-alkyl having 1 to 5 halogen atoms.

*A represents a heterocycle of the general formula (A-13)

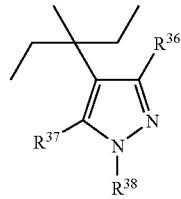

(A-13)

in which:
$R^{36}$ may be a hydrogen atom, a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl or an aminocarbonyl-$C_1$-$C_4$-alkyl;
$R^{37}$ may be a hydrogen atom, a halogen atom, a cyano group, a $C_1$-$C_4$-alkyl, a $C_1$-$C_4$-alkoxy, a $C_1$-$C_4$-halogenoalkoxy having 1 to 5 halogen atoms or a $C_1$-$C_4$-alkylthio; and
$R^{38}$ may be a hydrogen atom, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl, a $C_1$-$C_4$-halogenoalkoxy-$C_1$-$C_4$-alkyl having 1 to 5 halogen atoms or a phenyl optionally substituted by a halogen atom, a $C_1$-$C_4$-alkyl, a $C_1$-$C_4$-alkoxyalkyl or a nitro group.

* A represents a heterocycle of the general formula (A-14)

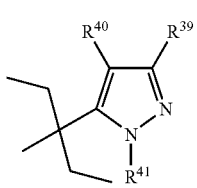

(A-14)

in which:
$R^{39}$ may be a hydrogen atom, a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl, or an aminocarbonyl-$C_1$-$C_4$-alkyl;
$R^{40}$ may be a hydrogen atom, a halogen atom, a cyano group, a $C_1$-$C_4$-alkyl, a $C_1$-$C_4$-alkoxy, a $C_1$-$C_4$-alkylthio or a $C_1$-$C_4$-halogenoalky having 1 to 5 halogen atoms;
$R^{41}$ may be a hydrogen atom, a phenyl, a benzyl, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl, a $C_1$-$C_4$-halogenoalkoxy-$C_1$-$C_4$-alkyl having 1 to 5 halogen atoms.

* A represents a heterocycle of the general formula (A-15)

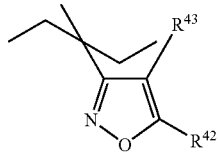

(A-15)

in which:
$R^{42}$ may be a hydrogen atom, a halogen atom, a $C_1$-$C_4$-alkyl or a $C_1$-$C_4$-halogenoalkyl having 1 to 5 halogen atoms; and
$R^{43}$ may be a halogen atom, a $C_1$-$C_4$-alkyl or a $C_1$-$C_4$-halogenoalkyl having 1 to 5 halogen atoms.

* A represents a heterocycle of the general formula (A-16)

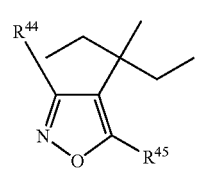

(A-16)

in which $R^{44}$ and $R^{45}$ may be the same or different and may be a hydrogen atom, a halogen atom, a $C_1$-$C_4$-alkyl, a $C_1$-$C_4$-halogenoalkyl having 1 to 5 halogen atoms, a phenyl optionally substituted by a halogen atom or a $C_1$-$C_4$-alkyl, or a heterocyclyl optionally substituted by a halogen atom or a $C_1$-$C_4$-alkyl.

* A represents a heterocycle of the general formula (A-17)

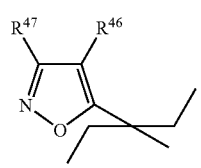

(A-17)

in which
$R^{46}$ may be a halogen atom, a $C_1$-$C_4$-alkyl or a $C_1$-$C_4$-halogenoalkyl having 1 to 5 halogen atoms. and
$R^{47}$ may be a halogen atom, a $C_1$-$C_4$-alkyl or a $C_1$-$C_4$-halogenoalkyl having 1 to 5 halogen atoms.

* A represents a heterocycle of the general formula (A-18)

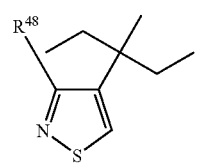

(A-18)

in which $R^{48}$ may be a halogen atom, a $C_1$-$C_4$-alkyl or a $C_1$-$C_4$-halogenoalkyl having 1 to 5 halogen atoms.

* A represents a heterocycle of the general formula (A-19)

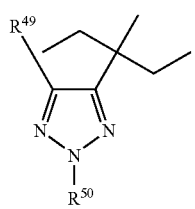
(A-19)

in which:
R$^{49}$ may be a halogen atom, a $C_1$-$C_4$-alkyl or a $C_1$-$C_4$-halogenoalkyl having 1 to 5 halogen atoms; and
R$^{50}$ may be a hydrogen atom, a $C_1$-$C_4$-alkyl, a $C_1$-$C_4$-halogenoalkyl having 1 to 5 halogen atoms, or a phenyl optionally substituted by a halogen atom or a $C_1$-$C_4$-alkyl.

* A represents a heterocycle of the general formula (A-20)

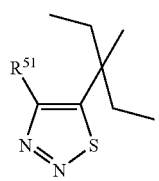
(A-20)

in which R$^{51}$ may be a halogen atom, a $C_1$-$C_4$-alkyl or a $C_1$-$C_4$-halogenoalkyl having 1 to 5 halogen atoms.

According to the present invention, A may also represent a six membered ring non-fused heterocycle. Specific examples of compounds prepared according to the process of the present invention where A is a six membered heterocycle include

* A represents a heterocycle of the general formula (A-21)

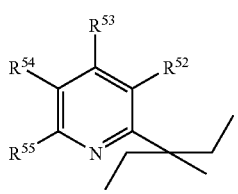
(A-21)

in which:
R$^{52}$ may be a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms or a $C_1$-$C_4$-halogenoalkoxy having 1 to 5 halogen atoms;
R$^{53}$, R$^{54}$ and R$^{55}$, which may be the same or different, may be a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkylsulphinyl or a $C_1$-$C_4$-alkylsulphonyl.

* A represents a heterocycle of the general formula (A-22)

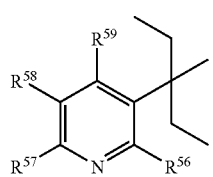
(A-22)

in which:
R$^{56}$ may be a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_5$-alkylthio, a $C_2$-$C_5$-alkenylthio a $C_1$-$C_4$-halogenoalkylthio having 1 to 5 halogen atoms, a $C_1$-$C_4$-halogenoalkoxy having 1 to 5 halogen atoms, a phenyloxy optionally substituted by a halogen atom or a $C_1$-$C_4$-alkyl, or a phenylthio optionally substituted by a halogen atom or a $C_1$-$C_4$-alkyl;
R$^{57}$, R$^{58}$ and R$^{59}$, which may the same or different, may be a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkylsulphinyl, a $C_1$-$C_4$-alkylsulphonyl or a N-morpholine optionally substituted by a halogen atom or a $C_1$-$C_4$-alkyl, or a thienyl optionally substituted by a halogen atom or a $C_1$-$C_4$-alkyl.

* A represents a heterocycle of the general formula (A-23)

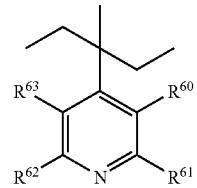
(A-23)

in which R$^{60}$, R$^{61}$, R$^{62}$ and R$^{63}$, which may be the same or different, may be a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms, a $C_1$-$C_4$-halogenoalkoxy having 1 to 5 halogen atoms, a $C_1$-$C_4$-alkylsulphinyl or a $C_1$-$C_4$-alkylsulphonyl.

* A represents a heterocycle of the general formula (A-24)

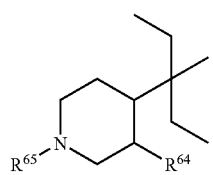
(A-24)

in which:
R$^{64}$ may be a halogen atom, a $C_1$-$C_4$-alkyl or a $C_1$-$C_4$-halogenoalkyl having 1 to 5 halogen atoms;
R$^{65}$ may be a hydrogen atom, a $C_1$-$C_4$-alkyl, a $C_1$-$C_4$-halogenoalkyl having 1 to 5 halogen atoms, a $C_1$-$C_6$- alkoxycarbonyl, a benzyl optionally substituted by 1 to 3 halogen atoms, a benzyloxycarbonyl optionally substituted by 1 to 3 halogen atoms or a heterocyclyl.

\* A represents a heterocycle of the general formula (A-25)

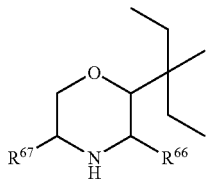

(A-25)

in which:
R$^{66}$ may be a halogen atom, a hydroxy group, a cyano group, a C$_1$-C$_4$-alkyl, a C$_1$-C$_4$-halogenoalkyl having 1 to 5 halogen atoms, a C$_1$-C$_4$-alkoxy, a C$_1$-C$_4$-alkylthio, a C$_1$-C$_4$-halogenoalkylthio having 1 to 5 halogen atoms or a C$_1$-C$_4$-halogenoalkoxy having 1 to 5 halogen atoms;
R$^{67}$ may be a hydrogen atom, a C$_1$-C$_4$-alkyl, a C$_1$-C$_4$-halogenoalkyl having 1 to 5 halogen atoms or a benzyl.

\* A represents a heterocycle of the general formula (A-26)

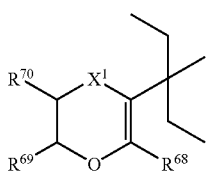

(A-26)

in which:
X$^1$ may be a sulphur atom, —SO—, —SO$_2$— or —CH$_2$—;
R$^{68}$ may be a C$_1$-C$_4$-alkyl or a C$_1$-C$_4$-halogenoalkyl having 1 to 5 halogen atoms; and
R$^{69}$ and R$^{70}$ may be the same or different and may be a hydrogen atom or a C$_1$-C$_4$-alkyl.

\* A represents a heterocycle of the general formula (A-27)

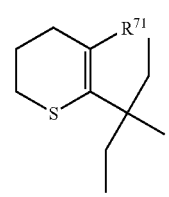

(A-27)

in which:
R$^{71}$ may be a C$_1$-C$_4$-alkyl or a C$_1$-C$_4$-halogenoalkyl having 1 to 5 halogen atoms;

\* A represents a heterocycle of the general formula (A-28)

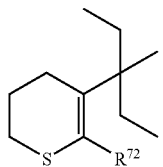

(A-28)

in which:
R$^{72}$ may be a C$_1$-C$_4$-alkyl or a C$_1$-C$_4$-halogenoalkyl having 1 to 5 halogen atoms.

\* A represents a heterocycle of the general formula (A-29)

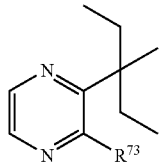

(A-29)

in which R$^{73}$ may be a halogen atom, a C$_1$-C$_4$-alkyl or a C$_1$-C$_4$-halogenoalkyl having 1 to 5 halogen atoms.

According to the present invention, A may also represent an optionally substituted phenyl group. Preferably, the present invention relates to the preparation of N-[2-(2-pyridinyl)ethyl]carboxamide derivative of general formula (I) in which A is a phenyl group and in which the different characteristics may be chosen alone or in combination as being:
A is substituted by 1 or 2 substituents. More preferably, A is substituted by 1 substituent.
each substituent is chosen, independently of the others, as being a hydrogen atom, a halogen atom, a C$_1$-C$_8$-alkyl or a C$_1$-C$_8$-halogenoalkyl having 1 to 5 halogen atoms. More preferably each substituent is chosen, independently of the others, as being chlorine or CF$_3$;
the phenyl moiety is substituted in ortho position.

The process of the present invention is particularly suitable for the preparation of:
N-{2-[3-chloro-5-(trifluoromethyl)-2-pyridinyl]ethyl}-2-trifluoromethylbenzamide;
N-{2-[3-chloro-5-(trifluoromethyl)-2-pyridinyl]ethyl}-2-iodobenzamide; or
N-{2-[3,5-dichloro-2-pyridinyl]ethyl}-2-trifluoromethylbenzamide.

The first step (step A) of the process according to the present invention comprises the reaction of a halogenobenzoyl derivative with aqueous R$^2$NH$_2$, in a R$^2$NH$_2$ aq./halogenobenzoyl derivative molar ratio of from 1 to 10, to provide a carboxamide derivative. Preferably, the R$^2$NH$_2$ aq./halogenobenzoyl derivative molar ratio of from 1 to 5.

Step A does not necessarily require the use of a solvent. Preferably, step A is conducted in the presence of a solvent. More preferably, the solvent is chosen as being a mixture of water and of an organic solvent. Suitable organic solvent includes tetrahydrofuran (THF) or toluene.

Step A does not necessarily require specific temperature conditions. Preferably, step A is conducted at a temperature of from 0° C. to reflux. More preferably, step A is conducted at a temperature of from 20° C. to reflux. Even more preferably step A is conducted at a temperature of from 60° C. to reflux.

The second step (step B) of the process according to the present invention comprises the reaction of a carboxamide derivative obtained in step A with an aldehyde group in an aldehyde group/carboxamide derivative molar ratio of from 1 to 10, in a polar solvent, at a temperature of from 20° C. to reflux, to provide a N-hydroxymethylcarboxamide derivative. Preferably, step B may be conducted in the following conditions, chosen alone or in combination:
the acyl group/carboxamide derivative molar ratio is of from 1 to 5;
the polar solvent is chosen as being water or an alcohol;
the reaction is conducted at reflux.

Step B is not necessarily conducted in the presence of a base. Preferably, step B is conducted in the presence of a mineral base in catalytic quantity. More preferably, the mineral base is chosen as being $K_2CO_3$, $Na_2CO_3$ or KOH.

The third step (step C) of the process according to the present invention comprises the reaction of a N-hydroxymethylcarboxamide derivative obtained in step B with $Ac_2O$ or AcCl in a $Ac_2O$ or AcCl/N-hydroxymethylcarboxamide derivative molar ratio of from 1 to 10, in an organic solvent, in the presence of a mineral or organic base, to provide a N-acetoxymethylcarboxamide derivative. Preferably, step C may be conducted in the following conditions, chosen alone or in combination:
the $Ac_2O$ or AcCl/N-hydroxymethylcarboxamide derivative molar ratio of from 1 to 5, more preferably of 1;
the reaction is conducted with $Ac_2O$;
the mineral base is chosen as being $Na_2CO_3$, $Li_2CO_3$, $K_2CO_3$, LiOAc, NaOAc or KOAc. More preferably, the mineral base is chosen as being $Na_2CO_3$ or NaOAc;
the organic base is chosen as being $NEt_3$ or N,N-dimethylaminopyridine, diazabicyclooctane (DABCO). More preferably, the organic base is chosen as being N,N-dimethylaminopyridine, diazabicyclooctane (DABCO);
$Ac_2O$ or AcCl is introduced in stoechiometric quantity;
the base is introduced in stoechiometric quantity or in catalytic quantity. More preferably, the base is introduced in catalytic quantity.

Step C does not necessarily require specific temperature condition. Preferably, step C is conducted at a temperature of from 0° C. to 50° C., more preferably at a temperature of from 5° C. to 35° C., even more preferably at room temperature.

The fourth step (step D) of the process according to the present invention comprises the reaction of a N-acetoxymethylcarboxamide derivative obtained in step C with a 2-pyridyl acetate derivative in a N-acetoxymethylcarboxamide derivative/2-pyridyl acetate derivative molar ratio of from 1 to 5, in an organic solvent, in the presence of a base, to provide a 2-pyridylethylcarboxamide derivative. Preferably, step D may be conducted in the following conditions, chosen alone or in combination:
the N-acetoxymethylcarboxamide derivative/2-pyridyl acetate derivative molar ratio is of 1;
the base is chosen as being a alkaline earth metal base, a alkali metal hydride base, a hydroxide base, an amide base, an alcoholate base, an acetate base, a carbonate base, a hydrogen carbonate base or a tertiary amine base. More preferably, the base is chosen as being hydrogen carbonate base which includes sodium hydride, sodium amide, lithium diisoproylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, ammonium carbonate, trimethylamine, triethylamine, tributyl-amine, N,N-dimethyl-aniline, N,N-di-methyl-benzylamine pyridine, N-methylpiperidine, N-methyl-morpholine, N,N-dimethylaminopyridine, diazabicyclooctane (DABCO), diazabicyclononene (DBN) or diazabicycloundecene (DBU). Even more preferably, the base is chosen as being sodium hydride, sodium hydroxide, sodium acetate, potassium carbonate, potassium hydroxide, triethylamine or potassium tert-butanolate;
the organic solvent is chosen as being an aliphatic solvent, an alicyclic solvent, an aromatic hydrocarbon solvent, a halogenated hydrocarbon solvent, an ether solvent, an amide solvent or an urea solvent. More preferably, the organic solvent is chosen as being petroleum ether, hexane, heptane, cyclo-hexane, methyl-cyclohexane, benzene, toluene, xylene, decalin, chloro-benzene, dichloro-benzene, trifluoromethyl benzene, dichloromethane, chloroform, carbon tetra-chloride, di-chloroethane, tri-chloro-ethane, diethyl ether, diisopropyl ether, methyl tert-butyl-ether, methyl tert-amyl-ether, dioxane, tetrahydrofuran, 1,2-di-methoxyethane, 1,2-di-ethoxy-ethane, anisole, N,N-dime-thyl-formamide, N,N-dimethyl-acetamide, N-methyl-formanilide, N-methyl-pyrrolidone, hexamethyl-phosphoric-triamide or 1,3-dimethyl-2-2-imidazolinone or N,N-dimethyl acetamide (DMAC). Even more preferably, the organic solvent is chosen as being tetrahydrofuran (THF) or N,N-dimethyl acetamide (DMAC).

Step D does not necessarily require specific temperature condition. Preferably, step D is conducted at a temperature of from 0° C. to 80° C., more preferably at a temperature of from 5° C. to 50° C.

The fifth step (step E) of the process according to the present invention comprises the decarboxylation of the 2-pyridylethylcarboxamide derivative obtained in step D into a compound of general formula (I) as defined above. Such a decarboxylation reaction may be performed by known methods. Such a decarboxylation reaction may for example be conducted according to the Krapcho reaction described in A.P. *Synthesis,* 1982, 805, 893, herein incorporated by reference.

The compound of general formula (I) according to the present invention can be prepared according to the above described process. It will nevertheless be understood that, on the basis of his general knowledge and of available publications, the skilled worker will be able to adapt this method according to the specifics of each of the compounds, which it is desired to synthesise.

Certain of the intermediates used for the preparation of compound of general formula (I) are novel. Therefore, the present invention also relates to novel intermediate compounds useful for the preparation of compound of general formula (I). Thus, according to the present invention, there is provided a compound of general formula (II)

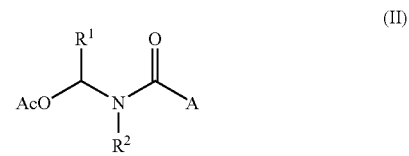

(II)

in which:

R[1], R[2] and A are as defined above; and

Ac represents an acetyl group.

According to the present invention, there is also provided a compound of general formula (III)

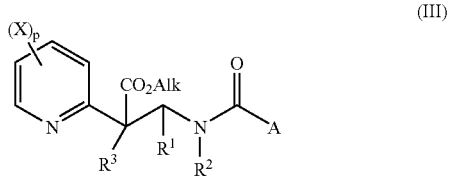

in which:

X, R[1], R[2], R[3], p and A are as defined above; and

Alk represents a $C_1$-$C_8$-alkyl group.

The present invention will now be illustrated with reference to the following examples.

Preparation of N-{2-[3-chloro-5-(trifluoromethyl)-2-pyridinyl]ethyl}-2-trifluoromethylbenzamide Step 1: Preparation of a 2-trifluoromethylbenzamide A two-necked round bottom flask equipped with a magnetic bar, a thermometer and an addition funnel was charged with 2-trifluoromethylbenzoic acid chloride (5.6 g, 26.9 mmol) and tetrahydrofuran (20 ml). An aqueous solution of ammonia 20% (20 ml, 107.6 mmol) was added at 20° C. during 15 min. The reaction mixture was agitated for two hours. The aqueous phase was then extracted 4 times with dichloromethane (4×50 ml), the organic phases were combined, dried over $MgSO_4$ and concentrated to the dryness under vacuum.

4.43 g of a white solid were obtained (isolated yield=87%).

NMR[1]H(CDCl$_3$, 300 MHz): 5.6-6.2 (br, 2H, $NH_2$); 7.5-7.8 (m, 4H, Haro)

Step 2: Preparation of a N-hydroxymethyl 2-trifluoromethylbenzamide

A two-necked round bottom flask equipped with a magnetic bar, a thermometer and a reflux condenser was charged with 2-trifluoromethylbenzamide (5.59 g, 29.6 mmol), water (35 ml), $K_2CO_3$ (0.118 g, 0.855 mmol) and formaldehyde (3.82 g, 127.3 mmol). The reaction mixture was heated at 100° C. for 15 hours. The aqueous phase was extracted 4 times with AcOEt (4×200 ml) at room temperature, the organic phases were mixed, dried over $MgSO_4$ and concentrated to the dryness under vacuum.

5.8 g of a white solid were obtained (isolated yield=90%).

NMR[1]H(CDCl$_3$, 300 MHz): 3.7 (t, 1H); 4.9 (t, 2H, $CH_2$); 6.8 (s, 1H); 7.5-7.7 (m, 4H, Haro).

Mass spectrum: [M+1]=220.

Step 3: Preparation of a N-acetoxymethyl 2-trifluoromethylbenzamide

EXAMPLE 1

A two-necked round bottom flask equipped with a magnetic bar, a thermometer and an addition funnel was charged with N-hydroxymethyl 2-trifluoromethylbenzamide (3 g, 13.7 mmol), $CH_2Cl_2$ (20 ml) and $NEt_3$ (1.93 ml, 13.7 mmol). The solution was cold to 5° C. and the $Ac_2O$ (1.93 ml, 13.7 mmol) was slowly added. The reaction mixture was agitated for two hours at 5° C. and 1 h at 20° C. The reaction mixture was washed with water, dried over $MgSO_4$ and concentrated to the dryness under vacuum.

3.5 g of a white solid were obtained (isolated yield=80%).

NMR[1]H(CDCl$_3$, 300 MHz): 2.1 (s, 3H, $CH_3$); 5.4 (d, 2H, $CH_2$); 7.0 (s, 1H); 7.5-7.7 (m, 4H, Haro).

EXAMPLE 2

A two-necked round bottom flask equipped with a magnetic bar, a thermometer and an addition funnel was charged with N-hydroxymethyl 2-trifluoromethylbenzamide (4.38 g, 20 mmol), MeCN (30 ml) and $K_2CO_3$ (5.53 g, 40 mmol). The solution was cold to 5° C. and the Ac2O (2.35 g, 23 mmol) was slowly added. The reaction mixture was agitated for 6 hours at 5° C. The reaction mixture was filtrated, the residue washed with a small amount of MeCN, and the filtrate concentrated to dryness under vacuum.

5 g of a white solid were obtained.

Purity (HPLC): 89.9%, giving an isolated yield of 86%.

Mass spectrum: [M+1]=262, base peak=202[M+1−AcOH].

EXAMPLE 3

A two-necked round bottom flask equipped with a magnetic bar, a thermometer and an addition funnel was charged with N-hydroxymethyl 2-trifluoromethylbenzamide (4.38 g, 20 mmol), MeCN (30 ml), $K_2CO_3$ (2.76 g, 20 mmol), and $NEt_3$ (0.2 g, 2 mmol). The solution was cooled to 5° C. and the Ac2O (2.35 g, 23 mmol) was slowly added. The reaction mixture was agitated for 2 hours at 5° C. and 3 hours at room temperature. The reaction mixture was filtrated, the residue washed with a small amount of MeCN, and the filtrate concentrated to dryness under vacuum.

5.38 g of a white solid were obtained. 0.32 g had to be substracted due to 2 mmol of $NEt_3$xAcOH, giving 5.06 g.

Purity (HPLC): 93.3%, giving an isolated yield of 90%.

EXAMPLE 4

A two-necked round bottom flask equipped with a magnetic bar, a thermometer and an addition funnel was charged with N-hydroxymethyl 2-trifluoromethylbenzamide (4.38 g, 20 mmol), MeCN (30 ml), $K_2CO_3$ (2.76 g, 20 mmol), and DABCO (1,4-diazabicyclo[2.2.2]octane) (0.224 g, 2 mmol). The solution was coold to 5° C. and the Ac2O (2.35 g, 23 mmol) was slowly added. The reaction mixture was agitated for 2 hours at 5° C. and 3 hours at room temperature. The reaction mixture was filtrated, the residue washed with a small amount of MeCN, and the filtrate concentrated to dryness under vacuum.

5.57 g of a white solid were obtained. 0.46 g had to be substracted due to 2 mmol of DABCOx2AcOH, giving 5.11 g.

Purity (HPLC): 92.8%, giving an isolated yield of 91%.

EXAMPLE 5

A two-necked round bottom flask equipped with a magnetic bar, a thermometer and an addition funnel was charged with N-hydroxymethyl 2-trifluoromethylbenzamide (4.38 g, 20 mmol), DMAC (30 ml) and $Na_2CO_3$ (2.12 g, 20 mmol). The Ac2O (2.35 g, 23 mmol) was slowly added at room temperature. The reaction mixture was agitated for 4 hours at room temperature. Then the reaction mixture was filtrated and the residue washed with a small amount of DMAC. To the filtrate was added water. This mixture was extracted with CH2Cl2 and the organic phase washed with water. The organic phase was dried over MgSO4 and concentrated under vacuum. and the filtrate concentrated under vacuum. 5.8 g of a colourless oil were obtained. Purity (HPLC): 53.75% (34.6% of DMAC), giving an isolated yield of 60%.

EXAMPLE 6

A two-necked round bottom flask equipped with a magnetic bar, a thermometer and an addition funnel was charged with N-hydroxymethyl 2-trifluoromethylbenzamide (4.38 g, 20 mmol), DMAC (30 ml) and $Li_2CO_3$ (1.478 g, 20 mmol). The Ac2O (2.35 g, 23 mmol) was slowly added at room temperature. The reaction mixture was agitated for 4 hours at room temperature. Then the reaction mixture was filtrated and the residue washed with a small amount of DMAC. To the filtrate was added water. This mixture was extracted with CH2Cl2 and the organic phase washed with water. The organic phase was dried over MgSO4 and concentrated under vacuum. and the filtrate concentrated under vacuum.

6.2 g of a colourless oil were obtained.
Purity (HPLC): 56% (18.9% of DMAC), giving an isolated yield of 66.5%.

EXAMPLE 7

A two-necked round bottom flask equipped with a magnetic bar, a thermometer and an addition funnel was charged with N-hydroxymethyl 2-trifluoromethylbenzamide (4.38 g, 20 mmol), DMAC (30 ml) and $Na_2CO_3$ (1.06 g, 10 mmol). The Ac2O (2.35 g, 23 mmol) was slowly added at room temperature. The reaction mixture was agitated for 4 hours at room temperature. Then the reaction mixture was filtrated and the residue washed with a small amount of DMAC. To the filtrate was added water. This mixture was extracted with CH2Cl2 and the organic phase washed with water. The organic phase was dried over MgSO4 and concentrated under vacuum. and the filtrate concentrated under vacuum.

5.45 g of a colourless oil were obtained.
Purity (HPLC): 85.45% (10.7% of DMAC) giving an isolated yield of 89%.

EXAMPLE 8

A two-necked round bottom flask equipped with a magnetic bar, a thermometer and an addition funnel was charged with N-hydroxymethyl 2-trifluoromethylbenzamide (4.38 g, 20 mmol), DMAC (30 ml) and $Na_2CO_3$ (0.53 g, 5 mmol). The Ac2O (2.35 g, 23 mmol) was slowly added at room temperature. The reaction mixture was agitated for 4 hours at room temperature. Then the reaction mixture was filtrated and the residue washed with a small amount of DMAC. To the filtrate was added water. This mixture was extracted with CH2Cl2 and the organic phase washed with water. The organic phase was dried over MgSO4 and concentrated under vacuum. and the filtrate concentrated under vacuum.

6.2 g of a colourless oil were obtained.
Purity (HPLC): 81.5% (15% of DMAC), giving an isolated yield of 97%.

EXAMPLE 9

A two-necked round bottom flask equipped with a magnetic bar, a thermometer and an addition funnel was charged with N-hydroxymethyl 2-trifluoromethylbenzamide (4.38 g, 20 mmol), DMAC (30 ml) and $Na_2CO_3$ (0.265 g, 2.5 mmol). The Ac2O (2.35 g, 23 mmol) was slowly added at room temperature. The reaction mixture was agitated for 4 hours at room temperature. Then the reaction mixture was filtrated and the residue washed with a small amount of DMAC. To the filtrate was added water. This mixture was extracted with CH2Cl2 and the organic phase washed with water. The organic phase was dried over MgSO4 and concentrated under vacuum. and the filtrate concentrated under vacuum.

6.6 g of a colourless oil were obtained.
Purity (HPLC): 63% (30.8% of DMAC), giving an isolated yield of 80%.

EXAMPLE 10

A two-necked round bottom flask equipped with a magnetic bar, a thermometer and an addition funnel was charged with N-hydroxymethyl 2-trifluoromethylbenzamide (4.38 g, 20 mmol), DMAC (30 ml) and $K_2CO_3$ (0.691 g, 5 mmol). The Ac2O (2.35 g, 23 mmol) was slowly added at room temperature. The reaction mixture was agitated for 4 hours at room temperature. Then the reaction mixture was filtrated and the residue washed with a small amount of DMAC. To the filtrate was added water. This mixture was extracted with CH2Cl2 and the organic phase washed with water. The organic phase was dried over MgSO4 and concentrated under vacuum. and the filtrate concentrated under vacuum.

6.55 g of a colourless oil were obtained.
Purity (HPLC): 63% (30.6% of DMAC), giving an isolated yield of 79%.

EXAMPLE 11

A two-necked round bottom flask equipped with a magnetic bar, a thermometer and an addition funnel was charged with N-hydroxymethyl 2-trifluoromethylbenzamide (4.38 g, 20 mmol), DMAC (30 ml) and NaOAc (1.641 g, 20 mmol). The $Ac_2O$ (2.35 g, 23 mmol) was slowly added at room temperature. The reaction mixture was agitated for 4 hours at room temperature. Then the reaction mixture was filtrated and the residue washed with a small amount of DMAC. To the filtrate was added water. This mixture was extracted with $CH_2Cl_2$, and the organic phase washed with water. The organic phase was dried over $MgSO_4$ and the filtrate concentrated under vacuum.

6 g of a colourless oil were obtained.
Purity (HPLC): 84.9% (8% of DMAC), giving an isolated yield of 97.5%.

EXAMPLE 12

A two-necked round bottom flask equipped with a magnetic bar, a thermometer and an addition funnel was charged with N-hydroxymethyl 2-trifluoromethylbenzamide (4.38 g, 20 mmol), DMAC (30 ml) and NaOAc (0.41 g, 5 mmol). The $Ac_2O$ (2.35 g, 23 mmol) was slowly added at room temperature. The reaction mixture was agitated for 4 hours at room temperature. Then the reaction mixture was filtrated and the residue washed with a small amount of DMAC. To the filtrate was added water. This mixture was extracted with $CH_2Cl_2$, and the organic phase washed with water. The organic phase was dried over $MgSO_4$ and the filtrate concentrated under vacuum.

6.1 g of a colourless oil were obtained.
Purity (HPLC): 85.3% (6.7% of DMAC), giving an isolated yield of 99.6%.

The purified product shows a melting point of 58-59° C.

Step 4: Preparation of a 3-chloro 5-trifluoromethyl 2-pyridyl ethyl(diethyl ester)2-trifluoromethylbenzamide Preparation of a 3-chloro 5-trifluoromethyl 2-pyridyl malonic acid ethyl ester

EXAMPLE 1

A two-necked round bottom flask equipped with a magnetic bar, a thermometer and an addition funnel was charged with 2,3-dichloro 5-trifluoromethylpyridyl (2.67 g, 12.4 mmol), NMP (20 ml) and NaOH (1.19 g, 31 mmol). Diethyl malonate (2.39 g, 14.8 mmol) was slowly added at 20° C. The reaction mixture was agitated for 20 hours. The reaction mixture was diluted with $CH_2Cl_2$ and washed with water. The organic phase was dried over $MgSO_4$ and concentrated to the dryness under vacuum.

3.57 g of a white solid were obtained (isolated yield=85%).
Mass spectrum: [M+1]=339.

EXAMPLE 2

A two-necked round bottom flask equipped with a magnetic bar, a thermometer and an addition funnel was charged with 2,3-dichloro 5-trifluoromethyl pyridine (5.4 g, 25 mmol), DMAC (20 ml) and NaOH (2.4 g, 40 mmol). Diethyl malonate (4.8 g, 30 mmol) was slowly added at 20° C. The temperature was raised to 70° C. and the reaction mixture was agitated for 3 hours at 70° C. Then the reaction mixture was cooled to room temperature and mixed with 200 ml of water. This mixture was extracted with CH2Cl2 and the organic phase washed with water. The organic phase was dried over MgSO4 and concentrated under vacuum.

9.66 g of an orange oil were obtained.
Purity (GC): 78.7% (16.3% DMAC), giving an isolated yield of about 89%.
Mass spectrum: [M+1]=340 ($^{35}Cl$)
Boiling point=87-90° C./0.06-0.07 mbar.
Melting point: 45.5-47° C. (cyclohexane).
NMR$^1$H(CDCl$_3$, 400 MHz): 1.30 (t, 6H, 2CH$_3$); 4.31 (m, 4H, 2CH$_2$); 5.25 (s, 1H, CH); 7.96 (d, 1H, Haro); 8.76 (d, 1H, Haro).

Preparation of a 3-chloro 5-trifluoromethyl 2-pyridyl ethyl (diethyl ester) 2-trifluoromethylbenzamide

EXAMPLE 1

A two-necked round bottom flask equipped with a magnetic bar, a thermometer and an addition funnel was charged with NaH (60% oil, 0.06 g, 1.47 mmol) and THF (10 ml). A solution of 3-chloro 5-trifluoromethyl 2-pyridyl malonic acid ethyl ester (0.321 g, 1.23 mmol) and N acetoxymethyl 2-trifluoromethylbenzamide (0.418 g, 1.23 mmol) in THF was added slowly. at 20° C. The reaction mixture was agitated for 1 hours. Water was slowly added and the aqueous phase was extracted with CH2Cl2. The organic phases were combined, dried over $MgSO_4$ and concentrated to the dryness under vacuum.

0.78 g of a white solid was obtained (isolated yield=88%).
NMR$^1$H(CDCl$_3$, 300 MHz): 1.3 (t, 6H, 2CH$_3$); 4.3 (m, 4H, 2CH$_2$); 4.6 (d, 2H, CH$_2$); 6.9 (t, 1H, CH); 7.4-7.6 (m, 4H, Haro); 8.0 (s, 1H, Haro); 8.6 (s, 1H, Haro).
Mass spectrum: [M+1]=541.

EXAMPLE 2

A round bottom flask equipped with a magnetic bar and a thermometer was charged with NaOH (0.24 g, 6 mmol), DMAC (10 ml), 3-chloro 5-trifluoromethyl 2-pyridyl malonic acid ethyl ester (1.67 g, 5 mmol) and N-acetoxymethyl 2-trifluoromethylbenzamide (1.31 g, 5 mmol). The reaction mixture was heated to 90° C. and agitated for 3 hours at this temperature. Then the mixture was cooled to room temperature. Water was slowly added and the aqueous phase was extracted with CH2Cl2. The organic phases were combined, dried over MgSO4 and concentrated to the dryness under vacuum.

2.74 g were obtained.
Purity (HPLC): 94.3%, giving an isolated yield of 95.5%.
Melting point: 76-80° C.

EXAMPLE 3

A round bottom flask equipped with a magnetic bar and a thermometer was charged with NaOH (0.04 g, 1 mmol), DMAC (10 ml), 3-chloro 5-trifluoromethyl 2-pyridyl malonic acid ethyl ester (1.67 g, 5 mmol) and N-acetoxymethyl 2-trifluoromethylbenzamide (1.31 g, 5 mmol). The reaction mixture was heated to 70° C. and agitated for 5 hours at this temperature. Then the mixture was cooled to room temperature. Water was slowly added and the aqueous phase was extracted with CH2Cl2. The organic phases were combined, dried over MgSO4 and concentrated to the dryness under vacuum.

2.88 g were obtained.
Purity (HPLC): 82.2%, giving an isolated yield of 87.5%.

EXAMPLE 4

A round bottom flask equipped with a magnetic bar and a thermometer was charged with NaOAc (0.41 g, 5 mmol), DMAC (10 ml), 3-chloro 5-trifluoromethyl 2-pyridyl malonic acid ethyl ester (1.67 g, 5 mmol) and N-acetoxymethyl 2-trifluoromethylbenzamide (1.31 g, 5 mmol). The reaction mixture was heated to 70° C. and agitated for 5 hours at this temperature. Then the mixture was cooled to room temperature. Water was slowly added and the aqueous phase was extracted with CH2Cl2. The organic phases were combined, dried over MgSO4 and concentrated to the dryness under vacuum.

2.76 g were obtained.
Purity (HPLC): 86.9%, giving an isolated yield of 88.7%.

Step 4: Preparation of a 3-chloro 5-trifluoromethyl 2-pyridyl ethyl(dimethyl ester) 2-trifluoromethylbenzamide Preparation of a 3-chloro 5-trifluoromethyl 2-pyridyl malonic acid methyl ester A two-necked round bottom flask equipped with a magnetic bar, a thermometer and an addition funnel was charged with DMAC (200 ml) and NaOH (12 g, 300 mmol). Then dimethyl malonate (20.4 g, 150 mmol) was added at a temperature of 65-70° C. After that 2,3-dichloro 5-trifluoromethylpyridine (27 g, 125 mmol) was added slowly at the same temperature. The temperature was raised to 90° C., and the reaction mixture was agitated for 1 hour at 90° C. The reaction mixture was cooled to room temperature and mixed with 250 ml of water. This mixture was extracted with CH2Cl2 and the organic phase washed with water. The organic phase was dried over MgSO4 and concentrated under vacuum.

39.2 g of an orange oil were obtained.
Purity (GC): 88.65% (5.8% DMAC), giving an isolated yield of about 89%.

Mass spectrum (GC/MS): 311 (M+, $^{35}$Cl); 276 (M—Cl, base peak).
NMR$^1$H(CDCl$_3$, 400 MHz): 3.83 (s, 6H, 2CH$_3$); 5.30 (s, 1H, CH); 7.97 (1H, Haro); 8.76 (d, 1H, Haro).
Boiling point: 91-94° C./0.18 mbar
Melting point: 49.5-50.5° C. (cyclohexane).

Preparation of a 3-chloro 5-trifluoromethyl 2-pyridyl ethyl(dimethyl ester) 2-trifluoromethylbenzamide A round bottom flask equipped with a magnetic bar and a thermometer was charged with NaOH (0.24 g, 6 mmol), DMAC (10 ml), 3-chloro 5-trifluoromethyl 2-pyridyl malonic acid methyl ester (1.56 g, 5 mmol) and N-acetoxymethyl 2-trifluoromethylbenzamide (1.31 g, 5 mmol). The reaction mixture was heated to 90° C. and agitated for 2 hours at this temperature. Then the mixture was cooled to room temperature. Water was slowly added and the aqueous phase was extracted with CH2Cl2. The organic phases were combined, dried over MgSO4 and concentrated to the dryness under vacuum.
2.5 g were obtained.
Purity (HPLC): 84.1%, giving an isolated yield of 82%.
Mass spectrum: [M+1]=513 ($^{35}$Cl).
Mass spectrum (GC/MS)=512 (M+, $^{35}$Cl), 173 (base peak).

Step 5: Preparation of a N-{2-[3-chloro-5-(trifluoromethyl)-2-pyridinyl]ethyl}-2-trifluoromethylbenzamide A two-necked round bottom flask equipped with a magnetic bar, a thermometer and a reflux condenser was charged with 3-chloro 5-trifluoromethyl 2-pyridyl ethyl (diethylester) 2-trifluoromethylbenzamide (0.610 g, 1.13 mmol), KCl (0.028 g, 0.37 mmol), HCl aq. 32% (0.17 ml, 1.5 mmol) and NMP (15 ml). The reaction mixture was heated at 180° C. 24 hours. At 20° C., water was added and the aqueous phase was extracted three times with CH$_2$Cl$_2$. The organic phases were combined, dried over MgSO$_4$ and concentrated to the dryness under vacuum.
0.5 g of a yellow solid was obtained (isolated yield=66%).
Mass spectrum: [M+1]=396.

The invention claimed is:
1. A process for the preparation of a N-[2-(2-pyridinyl) ethyl]carboxamide derivative of formula (I) or a salt thereof

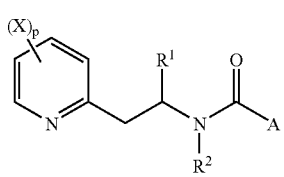

(I)

in which:
p is an integer equal to 1, 2, 3 or 4;
X is the same or different and is a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a (N—$C_1$-$C_8$-alkyl)oxycarbamoyl, a $C_1$-$C_8$-alkoxycarbamoyl, a (N—$C_1$-$C_8$-alkyl)-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkyl-sulphonyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl or a phenylamino;

$R^1$ is selected from the group consisting of a hydrogen atom, a $C_1$-$C_8$-alkyl, a $C_1$-$C_8$-halogenoalkyl having 1 to 5 halogen atoms and a $C_1$-$C_8$-alkoxycarbonyl;

$R^2$ is selected from the group consisting of a hydrogen atom and a cyclopropyl group; and A represents a phenyl group or a 5-, 6- or 7-membered non-fused heterocycle with one, two or three heteroatoms which may be the same or different, the heterocycle being linked by a carbon atom; each of this group being optionally substituted by one or more substituents independently selected from the group consisting of a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_9$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms and a $C_1$-$C_8$-alkylsulfonamide;

and the N-oxide of the 2-pyridine thereof;

said process comprising:

(A)-a first step according to reaction scheme 1:

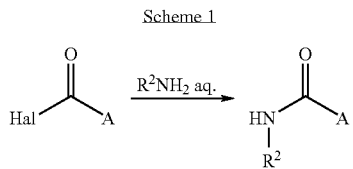

Scheme 1 in which:

A and $R^2$ are as defined above; and

Hal represents a halogen atom;

comprising the reaction of a halogenobenzoyl derivative with aqueous $R^2NH_2$, in a $R^2NH_2$ aq./halogenobenzoyl derivative molar ratio of from 1 to 10, to provide a carboxamide derivative;

(B)-a second step according to reaction scheme 2:

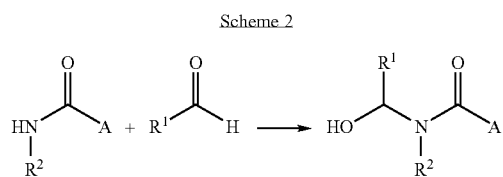

Scheme 2 in which:

$R^1$, $R^2$ and A are as defined above;

comprising the reaction of a carboxamide derivative obtained in step one with an aldehyde group in an aldehyde group/carboxamide derivative molar ratio of from 1 to 10, in a polar solvent, at a temperature of from 20° C. to reflux, to provide a N-hydroxymethylcarboxamide derivative;

(C)-a third step according to reaction scheme 3:

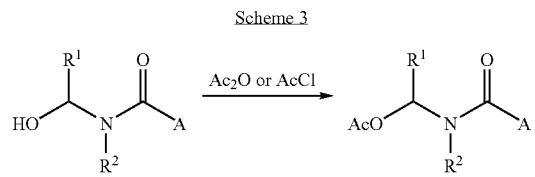

Scheme 3 in which:

$R^1$, $R^2$ and A are as defined above; and

Ac represents an acetyl group;

comprising the reaction of a N-hydroxymethylcarboxamide derivative obtained in step two with acetic anhydride ($Ac_2O$) or acetyl chloride (AcCl) in an $Ac_2O$ or AcCl/N-hydroxymethylcarboxamide derivative molar ratio of from 1 to 10, in an organic solvent, in the presence of a mineral or organic base, to provide a N-acetoxymethylcarboxamide derivative;

(D)-a fourth step according to reaction scheme 4:

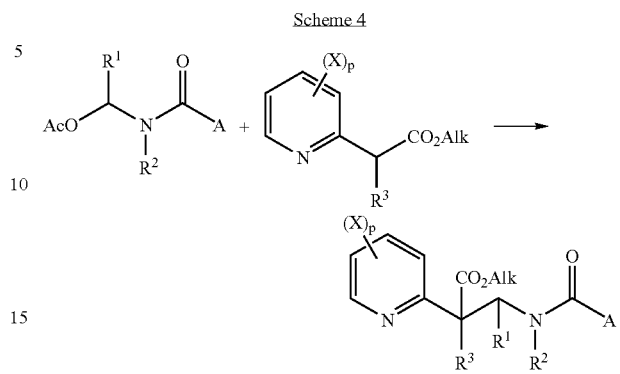

Scheme 4 in which:

X, $R^1$, $R^2$, p and A are as defined above;

Ac represents an acetyl group;

$R^3$ represents a hydrogen atom or $CO_2Alk$; and

Alk represents a $C_1$-$C_8$-alkyl group;

comprising the reaction of a N-acetoxymethylcarboxamide derivative obtained in step three with a 2-pyridyl acetate derivative in a N-acetoxymethylcarboxamide derivative/2-pyridyl acetate derivative molar ratio of from 1 to 5, in an organic solvent, in the presence of a base; to provide a 2-pyridylethylcarboxamide derivative; and (E)-a fifth step comprising the decarboxylation of the 2-pyridylethylcarboxamide derivative obtained in step four into a compound of formula (I).

2. The process of claim 1 wherein p is 2.

3. The process of claim 1 wherein X is independently selected from the group consisting of chlorine and $CF_3$.

4. The process of claim 1 wherein the 2-pyridyl moiety is substituted by X in the 3- and/or in the 5-position.

5. The process of claim 1 wherein $R^1$ is selected from the group consisting of a hydrogen atom, a methyl group, $CF_3$, $CHF_2$, $CClF_2$ and $CCl_3$.

6. The process of claim 1 wherein $R^2$ is a hydrogen atom.

7. The process of claim 1 wherein A is a phenyl group.

8. The process of claim 7 wherein A is substituted by one or two substituents.

9. The process of claim 8 wherein each substituent of A is independently selected from the group consisting of chlorine and $CF_3$.

10. The process of claim 7 wherein the A is substituted in ortho position.

11. The process of claim 1 wherein the compound of formula (I) is selected from the group consisting of:

N-{2-[3-chloro-5-(trifluoromethyl)-2-pyridinyl]ethyl}-2-trifluoromethylbenzamide;

N-{2-[3-chloro-5-(trifluoromethyl)-2-pyridinyl]ethyl}-2-iodobenzamide; and

N-{2-[3,5-dichloro-2-pyridinyl]ethyl}-2-trifluoromethylbenzamide.

12. The process of claim 1 wherein step A is conducted in the presence of a mixture of water and an organic solvent.

13. The process of claim 1 wherein step A is conducted at a temperature of from 0° C. to reflux.

14. The process of claim 1 wherein step B is conducted in the presence of a mineral base in catalytic quantity.

15. The process of claim 1 wherein step C is conducted at a temperature of from 0° C. to 50° C.

16. The process of claim 1 wherein, in step C, the base is introduced in catalytic quantity.

17. The process according to claim 1 wherein step D is conducted at a temperature of from 0° C. to 80° C.

* * * * *